United States Patent
Honjo et al.

(10) Patent No.: US 6,943,343 B2
(45) Date of Patent: Sep. 13, 2005

(54) CHEMICAL AGENT DETECTION APPARATUS AND METHOD

(75) Inventors: Shigeru Honjo, Otsuki (JP); Yasuaki Takada, Kiyose (JP); Hisashi Nagano, Hachioji (JP); Masumi Fukano, Yokohama (JP); Yasuo Seto, Kashiwa (JP); Teruo Itoi, Otone (JP); Kazumitsu Iura, Fuchu (JP); Mieko Kataoka, Kashiwa (JP); Kouichiro Tsuge, Kashiwa (JP)

(73) Assignees: Hitachi, Ltd., Tokyo (JP); President of National Research Institute of Police Science, Kashiwa (JP)

(*) Notice: Subject to any disclaimer, the term of this patent is extended or adjusted under 35 U.S.C. 154(b) by 52 days.

(21) Appl. No.: 10/628,139

(22) Filed: Jul. 29, 2003

(65) Prior Publication Data

US 2004/0084614 A1 May 6, 2004

(30) Foreign Application Priority Data

Nov. 6, 2002 (JP) ........................................ 2002-322680

(51) Int. Cl.⁷ ............................................. B01D 59/44
(52) U.S. Cl. ........................ 250/281; 250/282; 250/288
(58) Field of Search ................................. 250/288, 281, 250/282

(56) References Cited

U.S. PATENT DOCUMENTS

| | | | |
|---|---|---|---|
| 4,861,987 A | 8/1989 | Devienne | |
| 5,663,561 A | 9/1997 | Franzen et al. | |
| 5,965,882 A | 10/1999 | Megerle et al. | |
| 6,225,623 B1 | 5/2001 | Turner et al. | |
| 6,537,382 B1 * | 3/2003 | Bartram et al. | 134/7 |
| 6,639,215 B2 * | 10/2003 | Takada et al. | 250/288 |
| 6,727,400 B2 * | 4/2004 | Messier et al. | 588/315 |
| 6,770,877 B2 * | 8/2004 | Ohta et al. | 250/288 |
| 6,806,450 B2 * | 10/2004 | Nakashige et al. | 250/288 |

FOREIGN PATENT DOCUMENTS

| | | |
|---|---|---|
| EP | 0 423 454 A2 | 4/1991 |
| JP | A-6-302295 | 10/1994 |
| JP | A-2000-306545 | 11/2000 |
| JP | A-2001-147216 | 5/2001 |
| WO | WO 02/25265 | 3/2002 |

OTHER PUBLICATIONS

U.S. Appl. No. 10/426,718.

* cited by examiner

Primary Examiner—Kiet T. Nguyen
(74) Attorney, Agent, or Firm—Antonelli, Terry, Stout & Kraus, LLP

(57) ABSTRACT

An apparatus for detecting a chemical agent, capable of increasing a detection speed of a chemical agent, decreasing a false alarm rate, pinning down the kind of a chemical agent, and meeting specifications for unattended continuous monitoring equipment suitable for detecting sarin or soman. This detection apparatus comprises a sample introduction unit for introducing a sample, an ionizing unit for positively ionizing the sample from the sample introduction unit, a mass spectrometer unit for analyzing ions of the sample, and a computer for analyzing data, and is best suited for identifying a dangerous substance by detecting signals peculiar to chemical agents, such as sarin or soman.

17 Claims, 5 Drawing Sheets

CHEMICAL AGENT DETECTION APPARATUS AND METHOD

BACKGROUND OF THE INVENTION

This invention relates to a method and an apparatus for detecting chemical agents, and particularly to a method and an apparatus for detecting chemical agents by a mass spectrometer and APCI (atmospheric pressure chemical ionization), best suited for detecting isopropyl methylphosphonofluoridate (hereafter referred to as sarin) and pinacolyl methylphosphonofluoridate (hereafter referred to as soman).

In recent years, there has been demand for apparatuses for detecting chemical agents to cope with chemical terrorism incidents. For detection of chemical agents, the general method is analysis of chemical agents, and the prevailing analytical method is gas chromatography/mass spectrometry (GC/MS). Normally, there have been few cases where hazardous chemical agents were detected from samples, so that the presence of toxic chemical agents is proved by detection of decomposed substances which are likely to remain as residues.

As a conventional technology with another analytical apparatus for chemical agents, liquid chromatography/mass spectrometry (LC/MS) is well known, which is used to separate and analyze volatile or nonvolatile chemical compounds.

FIG. 9 is a diagram for explaining a schematic structure of an analytical apparatus using a liquid chromatography/mass spectrometry according to prior art. The analytical apparatus according to the prior art will be described in the following. In FIG. 9, 101 denotes a liquid chromatograph (LC), 102 denotes a connection tube, 103 denotes an ion source, 104 denotes a power supply for the ion source, 105 and 109 denote signal lines, 106 denotes a mass spectrometer, 107 denotes a vacuum system, 108 denotes an ion detector, and 110 denotes a data processor.

As shown in FIG. 9, the analytical apparatus using liquid chromatography/mass spectrometry according to the prior art comprises a liquid chromatograph (LC) 101 for separating samples into separate components, an ion source 103, controlled by the power supply 104 for the ion source, for generating ions derived from sample molecules, a mass spectrometer unit 106, evacuated by a vacuum system 107, for analyzing masses of generated ions, an ion detector 108 for detecting separated ions, and a data processor 110 for processing data. The mass spectrometer includes the ion source 103, the mass spectrometer unit 106, and the ion detector 108.

In the above description, sample liquid separated into respective components by liquid chromatograph (LC) 101 is introduced through the connection tube 102 into the ion source 103 that operates under atmospheric pressure. The ion source 103, controlled by the power supply for the ion source 104 through signal lines 105, generates ions derived from sample molecules in the sample liquid. Subsequently, the generated ions are introduced into the mass spectrometer unit 106 for mass spectrometry. The mass spectrometer unit 106 is evacuated by the vacuum pumping system 107. The ions subjected to mass spectrometry are detected by the ion detector 108. Detected signals are transmitted through the signal line 109 to the data processor 110 to generate analysis data, such as mass spectra and chromatograms.

As has been described, the mass spectrometer in the analytical apparatus needs to handle ions in vacuum and therefore requires an interface means to intervene between the spectrometer and the liquid chromatograph (LC). In other words, the LC is a device which handles large amounts of water and organic solvent under atmospheric pressure, whereas the mass spectrometer (MS) is a device for handling ions under high vacuum. For this reason, it has been considered difficult to directly connect them together.

The ion mobility spectrometer (IMS) method is used chiefly in combination with ionization of a sample by a radiation source to measure the mobility of its ions in an electric field, and this is the most prevalent in-situ detection method, and there are many applied products available in Europe and the U.S. Being applicable in a smaller configuration than GC/MS or LC/MS, the IMS method has found broad usages, including those to military specifications. However, because the IMS does not identify samples in terms of m/z (mass-to-charge ratio), detectors of IMS method have a rough indication of detection results and are limited to portable use with a warning attached to the effect that soldiers must wear protective masks when an alarm sounds.

As a conventional technology related to the IMS method, one which is described in U.S. Pat. No. 6,225,6223B1 is well known.

A U.S. Patent Application titled "Substance Detection Method and Substance Detection Apparatus" was filed on May 1, 2003, under Ser. No. 10/426718, in which substances, such as explosives, are vaporized and made into negative ions which are subjected to analysis.

The above-mentioned conventional GC/MS and LC/MS methods have a problem as follows. The technology of electron ionization (EI) applies strong energy to the substance itself to be detected and therefore the substance is liable to decompose, thus producing a multitude of fragment ions, for which reason detection devices by GC/MS have difficulty in generating ions of molecular weight of the substance or of a larger molecular weight, a fact which makes it difficult to identify the sample. The GC or LC process for separation of substances to be detected prolongs a detection time.

The problem with the above-mentioned IMS method is that it has difficulty in determining the kinds of chemical agents, and that because this method permits ready response to a wide range of chemical compounds, it is difficult to decide or identify samples to be detected, resulting in a high rate of false alarms.

SUMMARY OF THE INVENTION

The object of the present invention is to solve the problem with the conventional technology mentioned above, and provide a method and an apparatus for detecting chemical agents, capable of increasing a detection speed of chemical agents, decreasing a false alarm rate, pinning down the kinds of chemical agents, and meeting specifications for unattended continuous monitoring equipment suitable for detection of sarin or soman.

According to the present invention, the above object can be achieved by providing an ion source for introducing and positively ionizing a test sample by corona discharge, providing a mass spectrometer unit for analyzing the mass of ions from the ion source, which is carried out by sensing signals from chemical agents to be detected.

Further, the above object can be achieved by providing an ion source for introducing and positively ionizing a test sample by corona discharge, a mass spectrometer unit for analyzing the mass of ions generated by the ion source, and means for monitoring the ionic strength of ions from chemical agents to be detected.

Further, the above object can be achieved by providing an ion source for introducing and positively ionizing a test sample by corona discharge, a mass spectrometer unit for analyzing the mass of ions generated by the ion source, and means for monitoring the ion strength of ions each having m/z (mass-to-charge ratio) of chemical agents to be detected.

Further, the above object can be achieved by providing a sample introduction unit for introducing a test sample and heating the test sample, an ion source for ionizing a gas produced by heating by corona discharge, and a mass spectrometer unit for analyzing the mass of ions generated by the ion source, and detecting signals from chemical agents to be detected.

Further, the above object can be achieved by providing a sample introduction unit for introducing and heating a test sample, an ion source for ionizing a gas generated by heating by corona discharge, a mass spectrometer unit for analyzing the mass of ions generated by the ion source, and means for monitoring the ion strength of ions from chemical agents to be detected.

Further, the above object can be achieved by providing a sample introduction unit for introducing and heating a test sample, an ion source for ionizing a gas generated by heating by corona discharge, a mass spectrometer unit for analyzing the mass of ions generated by the ion source, means for monitoring the ion strength of ions each having m/z (mass-to-charge ratio) from a chemical agent to be detected.

In the foregoing description, the ion source is configured by using a counter-flow type atmospheric pressure chemical ionization (APCI) such that a test sample from the sample introduction unit is introduced to an area between the corona discharge generator unit and the mass spectrometer unit, and flows towards the corona discharge generator unit opposite the mass spectrometer unit.

The present invention including the above-mentioned means is capable of narrowing down the identity of chemical agents and reducing a false alarm rate, and therefore is best suited for detection of toxic chemical agents, such as sarin or soman. Peculiar to the present invention is the scheme of chemical detection using the counter-flow atmospheric pressure ionization (APCI) that a test sample introduced from the sample is supplied to a region between the corona discharge generator unit and the mass spectrometer unit, and flows towards the corona discharge unit opposite the mass spectrometer unit.

Other objects, features and advantages of the invention will become apparent from the following description of the embodiments of the invention taken in conjunction with the accompanying drawings.

DESCRIPTION OF THE INVENTION

Embodiments of a method and an apparatus for detecting chemical agents according to the present invention will be described in detail with reference to the accompanying drawings.

Figure 1:
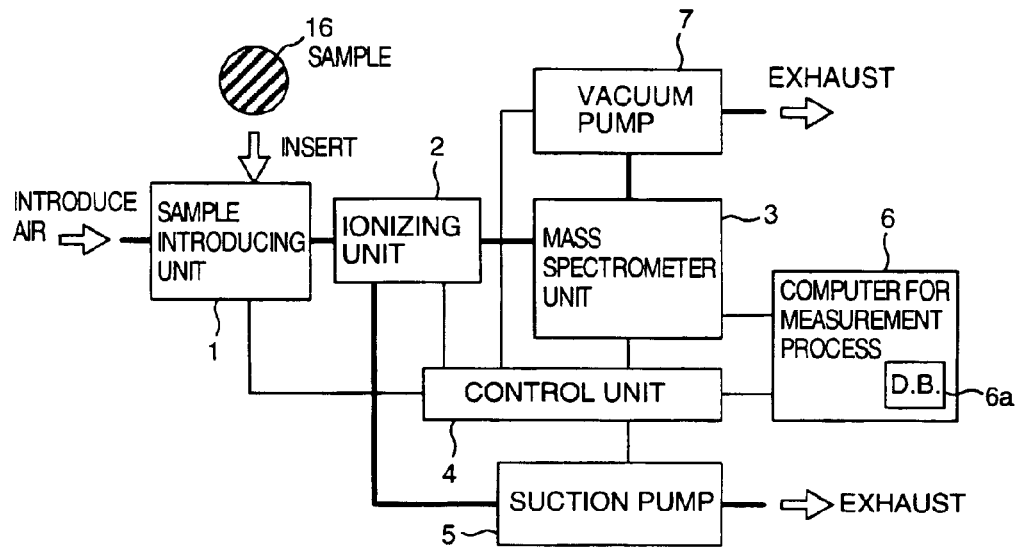
FIG. 1 is a block diagram showing a schematic structure of an apparatus for detecting chemical agents according to an embodiment of the present invention.

FIG. 1 is a block diagram showing a schematic structure of an apparatus for detecting chemical agents according to an embodiment of the present invention.

As shown in FIG. 1, an apparatus for detecting chemical agents according to an embodiment of the present invention comprises a sample introduction unit 1, an ionizing unit 2 as an ion source, a mass spectrometer unit 3, a control unit 4, a suction pump 5, a computer 6 for the measurement process, and a vacuum pump 7. In this chemical detection apparatus configured as described, a sample 16 having particles of a dangerous substance adhering to it is inserted into the sample introduction unit 1, and becomes a gas when it is heated by a heating device, not shown, mounted to the sample introduction unit 1. The sample in gaseous state is introduced through the flow path 81 indicated by a solid line while the sample in gaseous form carried by the atmospheric air is drawn into the ionizing unit 2 by the suction pump 5. The suction pump 5 performs a function to discharge the drawn-in atmospheric air and a function to vary the pumping quantity in a range of 0~2 liters/min. by a mass flow controller.

The test sample introduced into the ionizing unit 2 as the ion source is sent to a corona discharge region at the tip of a needle electrode for corona discharge to be described later, and a target component to be detected is positively ionized by a high positive voltage (about 2 kV~5 kV) applied to the needle electrode. Only the positive ions are introduced guided by an electric field that is generated in the range from the ionizing unit 2 to the mass spectrometer unit 3, pass through a first orifice provided at the ionizing unit 2, and are sent to the mass spectrometer unit 3. At this time, surplus substances other than ions and molecules that pass through the first orifice in the ionizing unit 2 are discharged from the ionizing unit 2 by the suction pump 5, and then exhausted to the outside of the apparatus by the suction pump 5. By keeping a sample introduction path between the sample introduction unit 1 and the ionizing unit 2, and the ionizing unit 2 at a high temperature, the sample can be prevented from being adsorbed to the internal wall of the introducing path or to the interior of the ionizing unit 2.

When detecting targets are chemical agents, such as sarin or soman, molecular ions are likely to become positive ions. For this reason, in this embodiment, positive ions are used as an analysis target.

The ions introduced into the mass spectrometer unit 3 pass through a differential exhaust portion in the mass spectrometer unit 3 depressurized by the vacuum pump 7, and are converged by an electrostatic lens system and its mass is analyzed by the mass spectrometer. The vacuum pump 7 has a function to keep the interior of the mass spectrometer chamber in a high vacuum state. The ions separated by the mass spectrometer are converted into electrons by a secondary electron multiplier in the mass spectrometer unit 3, and a resulting current signal is amplified by an amplifier and sent to the computer 6 for measurement process.

The computer 6 for measurement process processes a signal received from the mass spectrometer unit 3, and displays a relation between mass-to-charge ratio (m/z) and ion strength (a mass spectrum), a variation with time of the ion strength of a given m/z, and so on. A final display image may be a simplified diagram rather than a mass spectrum or mass chromatogram mentioned above. In other words, when a detection apparatus for chemical agents according to an embodiment of the present invention is used as an apparatus for detecting dangerous substances, it is only necessary for the apparatus to display whether or not a chemical substance was found which is problematical, namely, dangerous.

The control unit 4 performs on/off control of the functions of a detection apparatus, sets temperature, voltage, and vacuum pressure, and monitors status, and so on. The connections for these purposes are shown in FIG. 1 by thin control lines and data lines 82.

As mentioned above, according to an embodiment of the present invention, by the mass spectrometer 3, it is possible to analyze particles of a dangerous substance adhering to a sample 16, which is inserted into the sample introduction unit 1.

Figure 2:
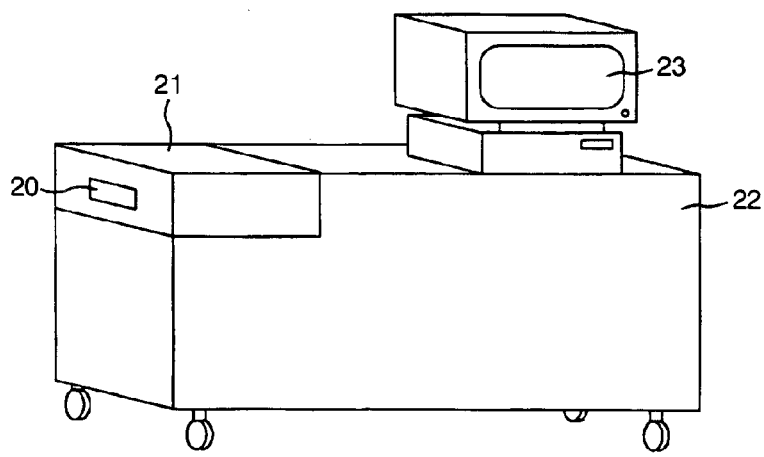
FIG. 2 is a perspective view showing an external appearance of a detection apparatus according to an embodiment of the present invention.

FIG. 2 is a perspective view of the external appearance of a detection apparatus according to an embodiment of the present invention. As shown in FIG. 2, the detection apparatus comprises a filter paper heating unit 21 with a filter paper entrance 20, an analyzer 22, and a display 23, and can be moved with casters under the bottom of the apparatus.

Normally, in a process that chemical agents are produced or transported, trace amounts of chemical agents adhere to hands or clothing of people who handle the chemical agents. When they handle their belongings, such as bags, chemical agents adhere to those belongings.

In the embodiments of the present invention, description is made in such a way that a soft material, such as cloth or filter paper (test paper is mentioned in the following description, but the material need not always be paper) is used to wipe the surface of a bag, for example, as a test sample (a detection object), and the chemical substance adhering to the test paper is analyzed. More specifically, test paper to which the chemical agents adheres is inserted through the filter paper entrance 20 to the filter paper heating unit 21. Since the test paper is heated in the filter paper heating unit 21, the chemical substance that adheres to the test paper evaporates, and the substance in gaseous state is analyzed by the analyzer 22. In the analyzer 22, the detection apparatus configured as described in FIG. 1 is accommodated, and database 6a in which information about signals from chemical agents is stored. When it is recognized from analysis results and information in the database 6a that signals peculiar to a chemical agent has been detected, the computer 6 for the measurement process displays an alarm on the display screen 23.

Figure 3:
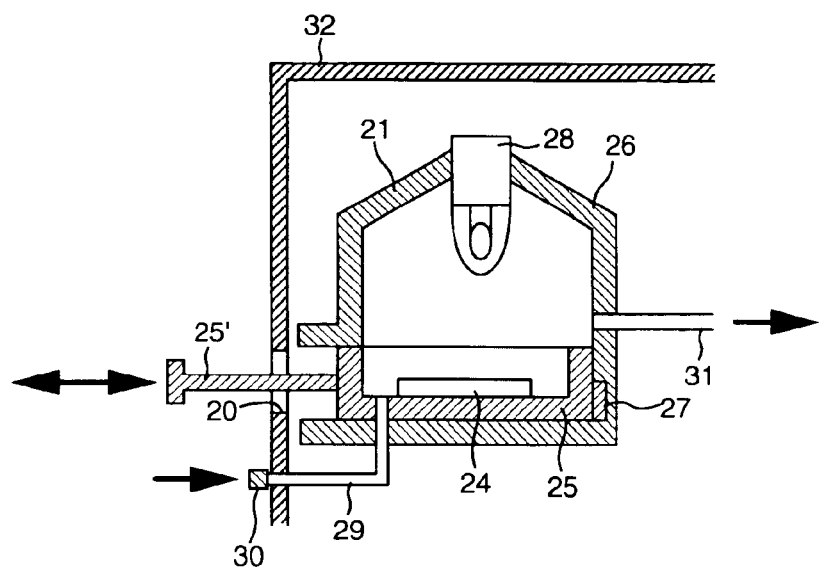
FIG. 3 is a sectional view showing a structural example of a filter paper heating unit (oven) shown in FIG. 2.

FIG. 3 is a sectional view showing a structural example of the filter paper heating unit (oven) 21 shown in FIG. 2. In FIG. 3, 24 denotes filter paper, 25 denotes a tray, 25' denotes a handle, 26 denotes a tray holder, 27 denotes a sensor, 28 denotes a halogen lamp, 29 denotes an air intake pipe, 30 denotes a filter, 31 denotes a sample introduction pipe, and 32 denotes a cover.

The filter paper heating unit (oven) 21 includes a tray holder 26, a halogen lamp 28 as a heat source mounted in the tray holder 26, and a tray 25 for loading filter paper 24. In the filter paper heating unit 21 structured as described, the tray 25 is pulled out by drawing the handle 25', and then filter paper 24, which is test paper by which the test object was wiped, is placed on the slide-type tray 25. The tray 25 on which filter paper 24 has been placed is inserted into the tray holder 26. When a sensor 27 detects the tray which has been pushed to a predetermined position, the halogen lamp 28 at the top of the tray holder 26 is turned on. The filter paper 24 is heated by heat waves from the halogen lamp 28, and the substance adhering to the filter paper 24 evaporates. The heating temperature should preferably be 100° C. or higher. The sample in gaseous state derived from the filter paper 24 is sent together with the air, which has entered from the air intake pipe 29, into the analyzer 22 through the sample introduction pipe 31.

The air intake pipe 29 may be provided with a filter 30 to remove dust or the like. Moreover, since the filter paper heating unit 21 is raised to a high temperature, a handle 25' and a heat-insulated cover 32 may be provided for safety. The sample introduction unit 1 may be of a type that directly introduces a test sample (detection object), drawn in from the outside, into the ionizing unit 2.

Figure 4:
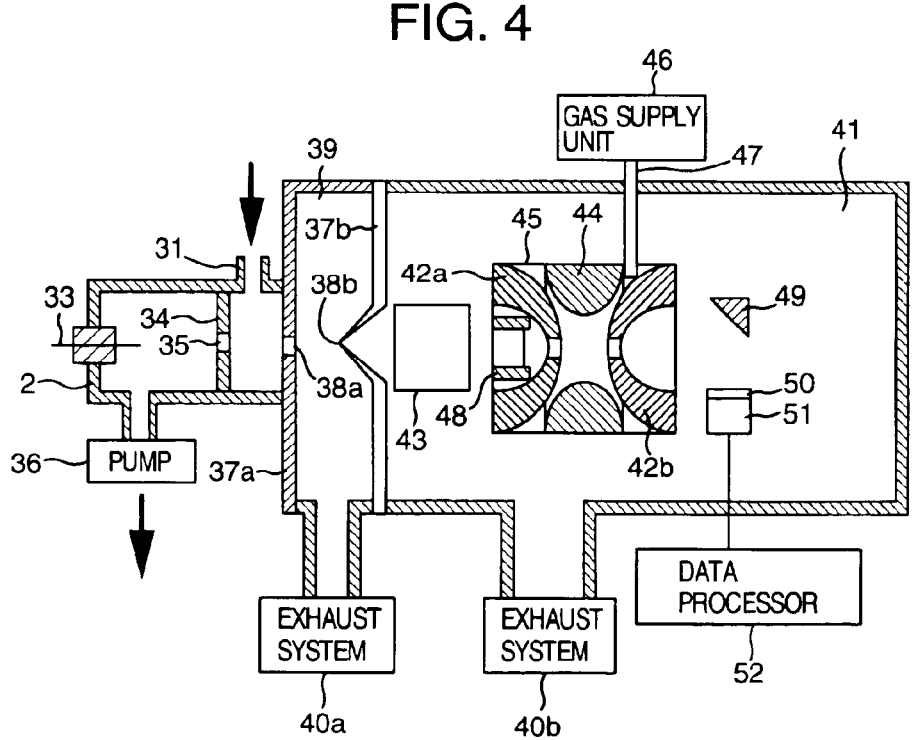
FIG. 4 is a block diagram showing a structural example of an ionizing unit and a mass spectrometer unit of the detection apparatus according to an embodiment of the present invention.

FIG. 4 is a block diagram showing a structural example of the ionizing unit and the mass spectrometer unit of the detection apparatus according to an embodiment of the present invention. In FIG. 4, 33 denotes a needle electrode, 34 denotes an opposite electrode, 35 denotes an opening, 36 denotes a suction pump, 37a and 37b denote electrodes each with an orifice, 38a denotes a first ion introduction orifice, 38b denotes a second ion introduction orifice, 39 denotes a differential exhaust portion, 40a and 40b denote exhaust systems, 41 denotes a vacuum section, 42a and 42b denote endcap electrodes, 43 denotes ion focusing lens, 44 denotes a ring electrode, 45 denotes a quartz ring, 46 denotes a gas supply unit, 47 denotes a gas introduction pipe, 48 denotes a gate electrode, 49 denotes a converter electrode, 50 denotes a scintillator, 51 denotes a photomultiplier, and 52 denotes a data processor.

In FIG. 4, in the ionizing unit 2, a high voltage is applied between the needle electrode 33 and the opposite electrode 34 and as a result corona discharge occurs in the vicinity of the tip of the needle electrode 33, so that nitrogen, oxygen and water vapor or the like in the atmospheric air are ionized, and they are called primary ions. The primary ions move towards the opposite electrode 34 guided by an electric field. The test sample drawn in from the sample introduction unit 1 through the sample introduction pipe 31 is supplied to an area between the opposite electrode 34 and the electrode 37a with an orifice, is made to flow towards the needle electrode 33 through the opening 35 in the opposite electrode 34 of the ionizing unit 2 by the suction pump 36, and reacts with the primary ions and thereby ionized.

Due to a potential difference of about 1 kV between the opposite electrode 34 and the electrode 37a with an orifice, the ions move towards the electrode 37a with the orifice, and guided through the orifice 38a into the differential exhaust portion 39. Because of adiabatic expansion that occurs in the differential exhaust portion 39, solvent molecules or the like adhere to the ions under test, and the ions increase in mass, which is called clustering. The ions produced by clustering appear as an unnecessary spectrum. To reduce clustering, it is desirable to heat the electrodes 37a and 37b each with an orifice with a heater, for example.

When an ionizing unit 2 of a structure shown in FIG. 4 is used, the ions generated by corona discharge move in the direction of the opposite electrode 34 owing to a potential difference between the needle electrode 33 and the opposite electrode 34, pass through the opening 35 and move towards the electrode 37a with the orifice. Because a test sample from the sample introduction unit is supplied between the opposite electrode 34 and the electrode 37a with the orifice, a reaction takes place between the primary ions and the test sample. Neutral molecules or the like produced by corona discharge flow from the opposite electrode 34 to the needle electrode 33 drawn by the suction pump 36, and thereby removed from the corona discharge region, and are less likely to flow to the area where an ionizing reaction takes place between the primary ions and the sample. In the manner described above, the area where the primary ions are generated by corona discharge is separated from the area where the sample is ionized by reaction with the primary ions, and radical neutral molecules produced by corona discharge are prevented from flowing into the ionizing area, thereby decreasing the decomposition of the sample in the ionizing area.

As has been described, according to an embodiment of the present invention, primary ions are generated by using corona discharge in the atmospheric air, and the test sample is ionized by using corona discharge by utilizing a chemical reaction between the primary ions and the test sample, by which the proportion of the test sample decomposed into fragments is reduced, and the proportion of molecular ions of the sample being detected is increased. This method is called atmospheric pressure chemical ionization method (APCI). In the positive ionization mode that generates positive ions by applying a high positive voltage to the needle electrode 33, the primary ions are mostly hydronium ion $[(H_3O)^+]$. The formula of a typical positive ionizing reaction where M is a molecule as a detection object and $H^+$ is a proton can be expressed as follows.

$$M+(H_3O)^+ \rightarrow (M+H)^+ + H_2O$$

The case where a sample is ionized has been described referring to an example that positive ions are generated, but some samples tend to generate negative ions. When negative ions are detected, a voltage of different polarity is applied.

The ions generated as described are introduced through the first introduction orifice 38a of the electrode 37a, then through the differential exhaust portion 39 evacuated by the exhaust system 40a, and through the second ion introduction orifice 38b of the electrode 37b, into the vacuum section 41 evacuated by the exhaust system 40b. A drift voltage is applied between the electrodes 37a and 37b. By this drift voltage, the ions introduced into the differential exhaust portion 39 are made to drift towards the second ion introduction orifice 38b, in which there two effects: (1) the ion permeability of the ion introduction orifice 38b is improved, and (2) the solvent molecules, such as water, adhering to the ions by clustering are detached from the ions by collision between the ions and the gas molecules remaining in the differential exhaust section 39. A voltage is further applied to the electrode 37b with an orifice. This voltage have an effect on energy (incident energy) when the ions pass through the opening of the endcap electrode 42a.

The ion trap efficiency of an ion trap mass spectrometer used in an embodiment of the present invention depends on the incident energy of the ions, and therefore the voltage applied to the electrode 37b is set so that the ion trap efficiency is high. The ions introduced into the vacuum section 41 are focused by the ion focusing lens 43, and then sent to the ion trap mass spectrometer including the endcap electrodes 42a, 42b and the ring electrode 44. The endcap electrodes 42a, 42b and the ring electrode 44 are held by the quartz ring 45.

A colliding gas, such as helium, is introduced from the gas supply unit 46 through the gas introduction pipe 47 into the mass spectrometer. The gate electrode 48 is provided to control timing of ion injection into the ion trap mass spectrometer. After mass spectrometry is over, the ions separated and led out of the mass spectrometer are detected by a detector formed by the converter electrode 49, the scintillator 50, and the photomultiplier 51. When an ion collides with the converter electrode 49 to which an ion-accelerating voltage is applied, charged particles are emitted from the surface of the converter electrode 49. This charged particle is detected by the scintillator 50, and the signal is multiplied by the photomultiplier 51 and detected. The detected signal is sent to the data processor 52. As the mass spectrometer, description has been made referring to the ion trap mass spectrometer as an example, but a quadrupole mass spectrometer may be used.

The data processor 52 identifies a positive ion having m/z from a chemical agent to be detected, such as sarin or soman, and obtains its signal strength, and thereby verifies whether sarin or soman as a target chemical agent has been detected. If sarin or soman has been detected, the data processor 52 causes the display 23 to notify an alarm and what has been detected. This indication of an alarm may be by generation of a high-pitched sound or by flashing of a red warning light.

Figure 5:
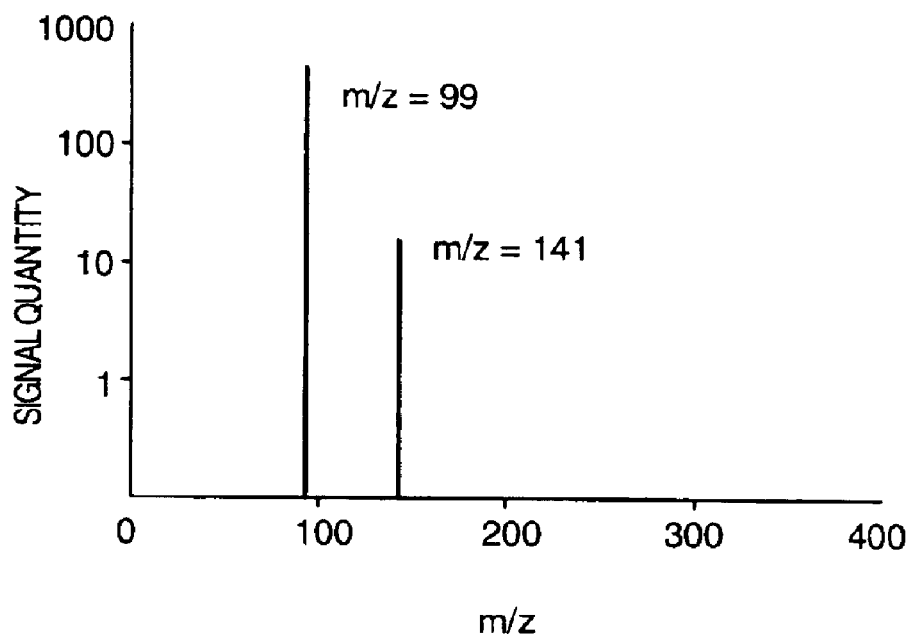
FIG. 5 is a diagram for explaining mass spectra of sarin, obtained according to an embodiment of the present invention.

FIG. 5 is a diagram for explaining a mass spectrum of sarin, obtained by the above-mentioned embodiment of the present invention. This is an example that the vapor of sarin was directly introduced into the sample introduction unit, in which positive ions were detected, and a drift voltage of 60V and the sample introduction unit and the ionizing unit were set at a temperature of 110° C.

As shown in FIG. 5, in this case, signals of m/z=99 and 141 were detected. Because sarin has a molecular weight MGB=140, the m/z=141 indicates that signals are from $(MGB+H)^+$ and m/z=99 indicates that signals are from decomposed substances of sarin. The m/z values of 99 and 141 of sarin as a detection object are previously stored in the database. By collating m/z values detected from test samples with stored data, decision is made whether the chemical agent being tested is sarin or not. When both signals of m/z=99 and 141 are detected, decision is made that sarin has been detected. This detection method makes it possible to reduce a false alarm rate. If by any chance a signal of m/z=99 (or 141) is issued from some other substance and only a signal of m/z=99 (or 141) is detected, a false alarm may be issued that sarin has been detected.

Figure 6:
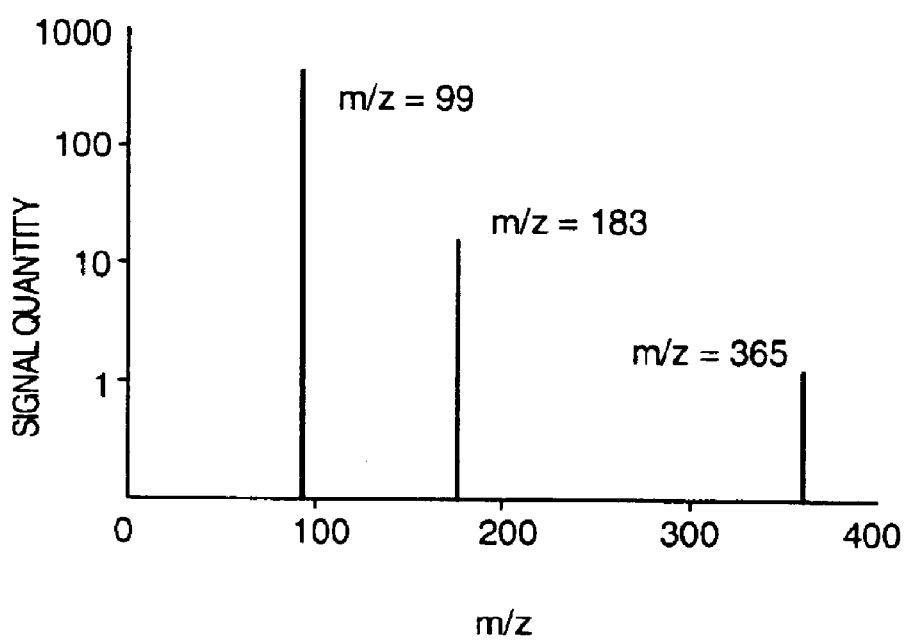
FIG. 6 is a diagram for explaining mass spectra of soman, obtained according to an embodiment of the present invention.

FIG. 6 is a diagram for explaining a mass spectrum of soman, obtained by the above-mentioned embodiment of the present invention. This is an example that the vapor of soman was directly introduced into the sample introduction unit, in which positive ions were detected, and a drift voltage of 60V and the sample introduction unit and the ionizing unit were set at a temperature of 110° C.

As shown in FIG. 6, in this case, signals of m/z=99, 183 and 365 were detected. Because soman has a molecular weight MGB=182, the m/z=183 indicates that signals are from (MGD+H)$^+$ and m/z=365 indicates that signals are from (2MGD+H)$^+$. The m/z=99 indicates that signals are from decomposed substances of soman. The m/z values of 99, 183 and 365 of soman as a detection object are previously stored in the database. When m/z values detected from test samples are collated with stored data, if, out of m/z=99, 183 and 365, two or three signals at m/z=99 are found, decision is made that soman has been detected. This detection method makes it possible to reduce a false alarm rate. If by any chance a signal of m/z=99 (or 183 or 365) is issued from some other substance and only a signal of m/z=99 (or 183 or 365) is detected, a false alarm may be issued that soman has been detected.

Figure 7:
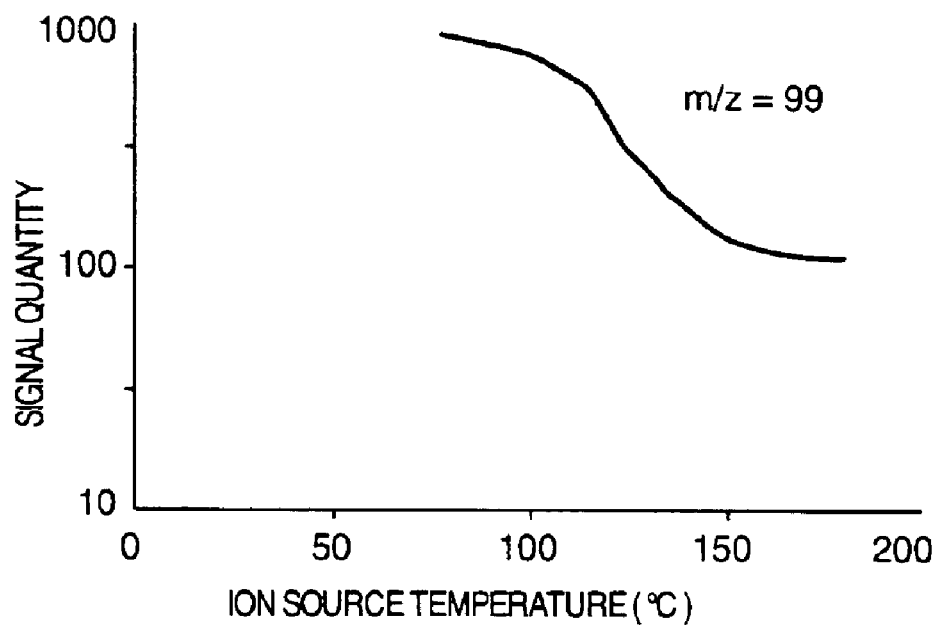
FIG. 7 is a diagram for explaining the ion source temperature dependence of signals with m/z=99 detected when samples of sarin or soman are introduced.

FIG. 7 is a diagram showing measured results of ion source temperature dependence of signals at m/z=99 detected when a sample of sarin or soman was introduced. As is clear from this diagram, when the ionizing unit 2 is raised higher than 100° C., the signal strength goes down till 150° C. This is considered because the decomposition of sarin or soman accelerates beyond 100° C. Therefore, by limiting the ion source temperature below 150° C., a greater quantity of signals can be obtained.

Figure 8:
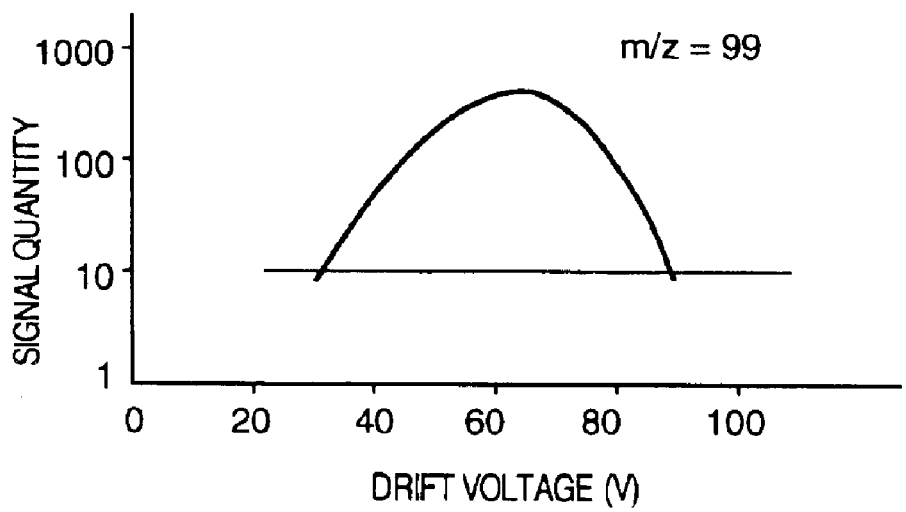
FIG. 8 is a diagram for explaining the drift voltage dependence of signals with m/z=99 detected when samples of sarin or soman are introduced.
Figure 9:
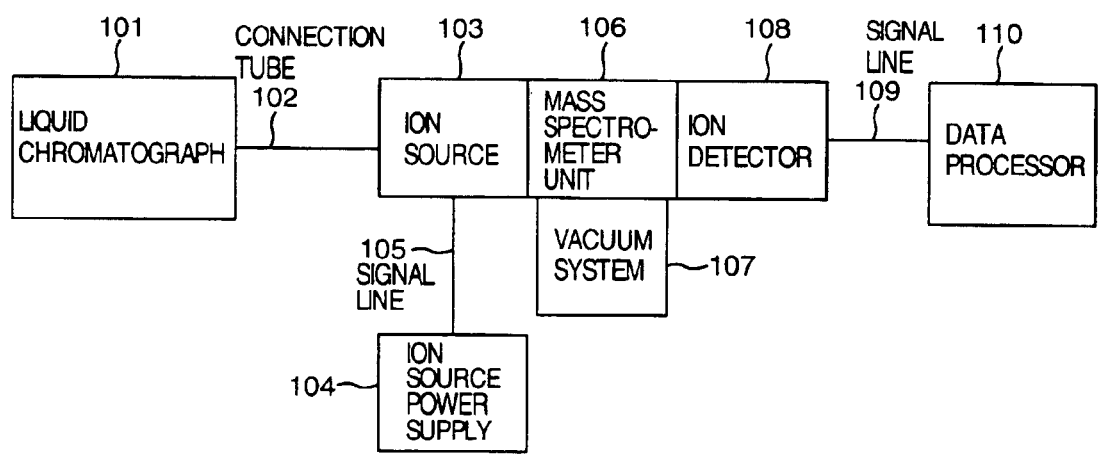
FIG. 9 is a diagram for explaining a schematic structure of an analytical apparatus using liquid chromatography/mass spectrometry according prior art.

FIG. 8 is a diagram showing measured results of drift voltage dependence of signals at m/z=99 detected when sarin or soman was introduced as a sample. As is apparent from FIG. 8, signals larger than background can be obtained when the drift voltage is higher than 30V and until 90V. What is meant by background here is that the level of signals with m/z=99 when neither sarin nor soman was not introduced as a sample. Decision is made whether or not sarin or soman is found while monitoring signals larger than background signals. Therefore, by setting the drift voltage in a range from 30V to 90V, a large quantity of signals can be obtained.

As has been described, according to the present invention, by drawing in a sample and examining the m/z by the analyzer unit of the detection apparatus [atmospheric pressure chemical ionization (APCI) with mass spectrometer (MS)], it is easy to verify whether or not there is sarin or soman.

It should be further understood by those skilled in the art that although the foregoing description has been made on embodiments of the invention, the invention is not limited thereto and various changes and modifications may be made without departing from the spirit of the invention and the scope of the appended claims.

What is claimed is:

1. An apparatus for detecting chemical agents comprising:
   a sample introduction unit for introducing a test sample to an ion source without passing through a separation system;
   said ion source positively ionizing said introduced sample by corona discharge to produce positive ions;
   a mass spectrometer unit for analyzing the mass of said positive ions produced in said sample ionized by said ion source; and
   a measurement process unit for measuring positive ions separated by said mass spectrometer unit, and for, on the basis of a signal of measurement results derived from a chemical agent to be detected, deciding whether said test sample is said chemical agent to be detected.

2. A detection apparatus according to claim 1, wherein a decision in said measurement process unit is made by monitoring the strength of ions derived from said chemical agent to be detected.

3. A detection apparatus according to claim 1, wherein a decision in said measurement process unit is made by monitoring the strength of ions having a value of m/z (mass-to-charge ratio) derived from said chemical agent to be detected.

4. A detection apparatus according to claim 3, wherein said measuring process unit includes a database having said value of m/z stored therein.

5. A detection apparatus according to claim 4, wherein said values of m/z are 99 and 141.

6. A detection apparatus according to claim 4, wherein said values of m/z are 99, 183, and 365 and wherein said decision is made by at least two of said values.

7. A detection apparatus according to claim 1, wherein said ion source has a needle electrode and an opposite electrode for generating corona discharge.

8. A detection apparatus according to claim 7, wherein a sample introduced from said sample introduction unit is made to flow from said opposite electrode towards said needle electrode.

9. A detection apparatus according to claim 8, wherein said opposite electrode has an opening, and said sample introduced from said sample introduction unit is guided through said opening to said ion source, and is made to flow towards said needle electrode, and discharged to the outside by suction pump.

10. A detection apparatus according to claim 8, wherein in a process that primary ions generated by corona discharge occurring between said needle electrode and said opposite electrode are moved towards the opening of said opposite electrode, ions generated by an ionizing reaction of said sample with said primary ions are sent through said opening of said opposite electrode to said mass spectrometer unit.

11. A detection apparatus according to claim 1, wherein said ion source uses atmospheric pressure chemical ionization.

12. A detection apparatus according to claim 1, wherein the temperature of said ion source is set at 150° C. or lower.

13. A detection apparatus according to claim 1, wherein in a differential exhaust portion of said mass spectrometer unit, a drift voltage of 30V~90V is applied between an electrode with an orifice on an ion entrance side of said differential exhaust portion and an electrode with an orifice on an ion outlet side of said differential exhaust portion.

14. A detection apparatus according to claim 1, wherein said chemical agent to be detected is isopropyl methylphosphonofluoridate or pinacolyl methylphosphonofluoridate.

15. An apparatus for detecting a chemical agent comprising:
   a sample introduction unit for introducing, heating and vaporizing a test sample so as to introduce said vaporized test sample to an ion source without passing through a separation system;
   said ion source positively ionizing said introduced vaporized test sample so as to produce positive ions by corona discharge;
   a mass spectrometer unit for analyzing the mass of positive ions generated by said ion source; and
   a measurement process unit for measuring said positive ions separated by said mass spectrometer unit, and for determining whether or not said test sample is a chemical agent to be detected based on a signal of a measured result derived from a chemical agent to be detected.

16. A method for detecting a chemical agent comprising the steps of:
   introducing a test sample to an ionizer without passing through a separation system;
   positively ionizing the test sample introduced to the ionizer by corona discharge to thereby generate positive ions;

performing analyzing of the mass of generated positive ions; and measuring the positive ions analyzed by mass spectrometry and determining based on a signal of a measured result derived from a chemical agent to be detected whether or not said sample is the chemical agent to be detected.

17. A method for detecting a chemical agent comprising the steps of:

heating and vaporizing a test sample which is introduced to an ionizer without passing through a separation system;

positively ionizing the vaporized test sample introduced to the ionizer by corona discharge to thereby generate positive ions;

performing analyzing of the mass of generated positive ions; and measuring the positive ions analyzed by mass spectrometry and determining based on a signal of a measured result derived from a chemical agent to be detected whether or not said vaporized sample is the chemical agent to be detected.

* * * * *